(12) United States Patent
Gradl

(10) Patent No.: US 8,323,321 B2
(45) Date of Patent: Dec. 4, 2012

(54) IMPLANT AND BONE SCREW HAVING INTERLOCKING CAMS

(75) Inventor: Georg Gradl, Börgerende (DE)

(73) Assignee: M.O.R.E. Medical Solutions GmbH (DE)

( * ) Notice: Subject to any disclaimer, the term of this patent is extended or adjusted under 35 U.S.C. 154(b) by 0 days.

(21) Appl. No.: 13/126,909

(22) PCT Filed: Oct. 23, 2009

(86) PCT No.: PCT/EP2009/063981
§ 371 (c)(1),
(2), (4) Date: Jun. 17, 2011

(87) PCT Pub. No.: WO2010/049361
PCT Pub. Date: May 6, 2010

(65) Prior Publication Data
US 2011/0238122 A1    Sep. 29, 2011

(30) Foreign Application Priority Data

Oct. 31, 2008 (DE) .................. 10 2008 043 370

(51) Int. Cl.
*A61B 17/80* (2006.01)
(52) U.S. Cl. ........ 606/291; 606/289; 606/305; 606/308; 411/399
(58) Field of Classification Search .................. 606/289, 606/291; 411/85, 399
See application file for complete search history.

(56) References Cited

U.S. PATENT DOCUMENTS

| | | | | |
|---|---|---|---|---|
| 1,151,861 A * | 8/1915 | Brumback | ..................... | 411/399 |
| 5,275,601 A * | 1/1994 | Gogolewski et al. | ......... | 606/291 |
| 6,129,730 A * | 10/2000 | Bono et al. | ..................... | 606/291 |
| 6,623,486 B1 * | 9/2003 | Weaver et al. | ................. | 606/281 |
| 6,730,091 B1 * | 5/2004 | Pfefferle et al. | ................. | 606/70 |
| 6,854,942 B1 * | 2/2005 | Hargis | ........................... | 411/369 |
| 6,955,677 B2 * | 10/2005 | Dahners | ........................ | 606/287 |
| 7,137,987 B2 * | 11/2006 | Patterson et al. | .............. | 606/291 |
| 7,250,053 B2 * | 7/2007 | Orbay | ............................ | 606/291 |
| 7,637,928 B2 * | 12/2009 | Fernandez | ..................... | 606/289 |
| 7,695,472 B2 * | 4/2010 | Young | ............................ | 606/70 |
| 7,766,948 B1 * | 8/2010 | Leung | ........................... | 606/305 |
| 7,776,076 B2 * | 8/2010 | Grady et al. | ................... | 606/291 |
| 7,951,176 B2 * | 5/2011 | Grady et al. | ................... | 606/280 |
| 8,216,284 B2 * | 7/2012 | Leung | ........................... | 606/289 |
| 2003/0171754 A1 * | 9/2003 | Del Medico | .................... | 606/69 |
| 2004/0073218 A1 * | 4/2004 | Dahners | ........................ | 606/69 |

* cited by examiner

*Primary Examiner* — Andrew Yang
(74) *Attorney, Agent, or Firm* — Wood, Phillips, Katz, Clark & Mortimer

(57) ABSTRACT

The invention relates to a fixation device for bones, consisting of all implant (1; 11), having at least one through hole (2; 12), to be fastened to the bone, and of at least one bone screw (3; 13) to be fastened in said through hole (2; 12), fastening elements (5; 15) being arranged in the through hole (2; 12) and at the top end of the bone screw (3; 13) and engaging with each other. In order to allow various angular positions of the bone screw (3; 13) relative to the implant (1; 11) without cold welding, interlocking earns (6, 7; 16, 17) are arranged on the associated surfaces of the through hole (2; 12) and the bone screw (3; 13) as the fastening elements (5; 15).

3 Claims, 1 Drawing Sheet

IMPLANT AND BONE SCREW HAVING INTERLOCKING CAMS

The invention relates to a fixation device for bones comprising an implant to be fastened to the bone having a least one through hole, and at least one bone screw to be fastened in said through hole, with fastening elements being arranged in the through hole and at the upper end of the bone screw which engage with each other.

In order to treat fractures mainly at the joint-bearing ends of the long tubular bones implants in the form of steel or titanium plates are required which ideally can be fixed with bone screws. These are firmly attached to the implant. This is due to the fact that the bone screw and the implant have threads complementing each other. After screwing in the bone screw into the implant a angle-stable fixation device is formed, however in the event of removal of an implant the bone screw can often not be removed from right angle position without considerable force being applied.

This brings about greater rigidity of osteosynthesis which comes into its own due to the low rate of implant failure. However, one problem is that the bone screw can only be inserted into the corresponding implant at a certain angle, namely the angle of the thread. The prerequisite for this is that the implant has to be optimally adapted/bent to fit a bone. Inter-individual differences in the anatomy of humans and differences in the fracture geometry therefore have to be disregarded.

In recent years the monoaxial angular stability of conventional implants has been converted into a polyaxial angular stability, which is achieved through the surgeon cutting a thread when screwing in the bone screw. A hard titanium alloy is chosen for the screw here, whereas for the through hole a soft material or a soft alloy is selected. The drawback of this is the incurred material wear.

In a variant in accordance with DE 10 2005 015 496 A1 the thread is cut in various directions in the through hole in the implant so that the surgeon can choose from five different angles. However, this requires a considerable amount of work during the manufacturing of the implant.

In monoaxially angle-stable implants there is the danger when screwing in the threaded bone screw into the threaded through hole of the implant of cold welding taking place if tilting occurs when screwing the bone screw into the thread of the implant and the bone screw no longer fitting precisely into the complementary thread of the implant. This causes deformations leading to very firm fixation of the bone screw in the threaded hole. This is undesirable and makes the subsequent removal of the bone screw very difficult in the event of having to remove an implant. All other polyaxial angular stability solutions also result in deformation of the threads, even if this is not planned, which only occurs at certain points as the threads are not formed completely, but only consist of thread fragments.

A fixation device of the aforementioned type is previously known from DE 198 58 889 B1. In this case the fastening elements are designed on the bone screw as a preformed thread and in the through hole of the implant as a circular projection. The bone screw can be screwed into the implant at various angular positions in relation to the axis of the through hole. In the case of this fixation device too there is the danger of cold welding occurring between the bone screw and the implant.

The aim of the invention it to create a fixation device of the aforementioned type in such a way that various angular positions of the bone screw relative to the implant are possible without cold welding taking place.

To achieve this, the invention envisages that interlocking cams are arranged on the associated surfaces of the through hole and the bone screw. Screwing in of the bone screw provided with cams into the through hole of the implant, which also has cams, is possible at various angular positions of the bone screw relative to the implant, i.e. monoaxially and also polyaxially without cold welding occurring between the cams on both sides.

In a particularly preferred manner the cams are formed of thread elements. These can be formed of individual threads which are cut through in an axially-parallel manner and thereby form individual cams.

In a particularly preferred manner the bone screw has at least two threads, whereby the axis of one thread runs coaxially to the axis of the bone screw and the axis of the second thread runs at an acute angle to the axis of the bone screw. This solution, in which on a bone screw threads are applied/cut in different directions, results in a fragmentation of the thread which allows both monoaxiality as well as polyaxiality of the bone screw relative to implant and also prevents cold welding. This is achieved in that in a first working stage the first thread is cut on the bone screw and the thread cutter is then tilted in order to form the second thread at a different, acute angle to the axis of the bone screw. This leads to thread fragmentation. The resulting cams formed by the thread remnants do not cause cold welding when the bone screw and implant are joined. Multiple threads are applied to the bone screw. The through hole in the implant does not require a polyaxial thread.

In an even more advantageous embodiment of the invention at least one thread is provided in the through hole of the implant, whereby to achieve the necessary stability two threads are expediently provided which are designed to form thread fragments. The second thread can also be formed as a ring without a thread pitch.

In a yet further embodiment of the invention the through hole in the implant is conical on both sides of the implant in order to allow polyaxial fastening of the bone screw in the implant at various acute angles.

The invention will be explained in more detail below with the aid of two forms of embodiment, shown in the drawings, of fixation devices for bones comprising an implant and a bone screw.

Figure 1:
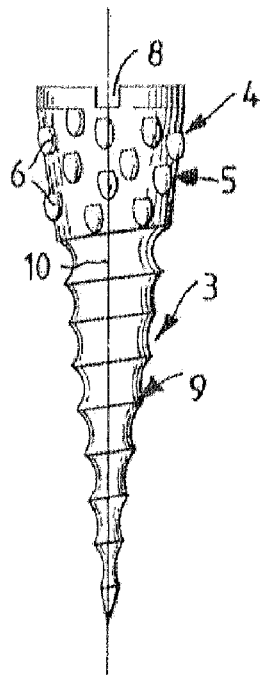
FIG. 1 shows a view of the bone screw in the first form of embodiment.
Figure 2:
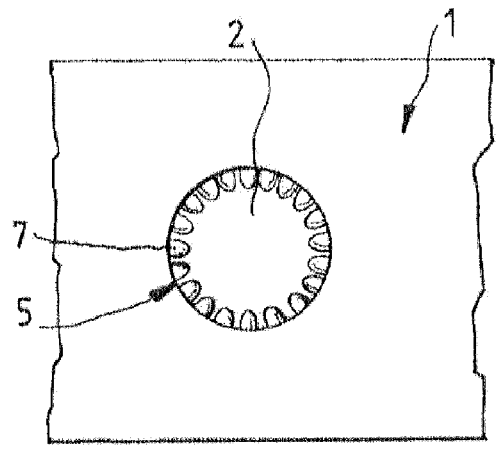
FIG. 2 shows a partial view of the implant for the bone screw in the first form of embodiment in accordance with FIG. 1.

In accordance with FIGS. 1 and 2 the first form of embodiment of the fixation device for bones consists of an implant 1 for attaching to the bone and made of a soft metallic material with at least one through hole 2, and at least one bone screw 3, preferably made of titanium or a titanium alloy, for fastening in the through hole 2. Arranged in the through hole 2 and on the upper end of the bone screw 3 formed by the head 4 are interlocking fastening elements 5. These are in the form of cams 7 on the associated surfaces of the through hole 2 and cams 6 on the bone screw 3.

As can be seen in FIG. 1, the head 4 on the upper end of the bone screw 3 is conical and is provided with a slit 8 for inserting a tool. In the direction of the axis 10 the shaft 9 is provided with a special screw thread for the bone.

The through hole 2 in the implant 1 can be conical on both sides of the implant 1.

Figure 3:
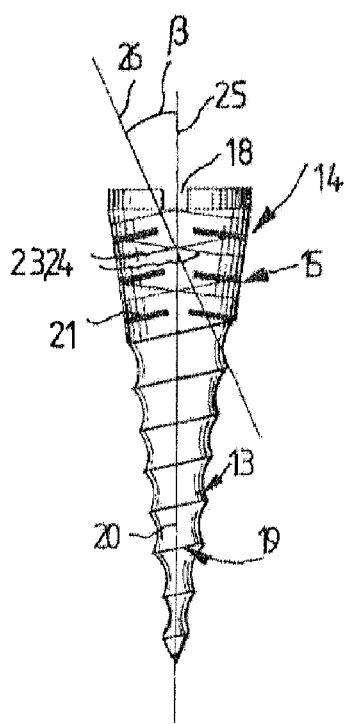
FIG. 3 shows a view of the bone screw in the second form of embodiment and FIG. 4 shows a cross-section through the through hole in the implant for the bone screw in accordance with FIG. 3.
Figure 4:
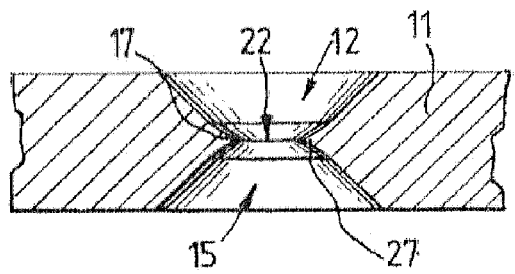

In the second form of embodiment shown in FIGS. 3 and 4 the cams 16, 17 provided as fastening elements 15 are formed from thread elements 21, 22. On its conical head 14 the bone screw 13 has at least two threads 23, 24, whereby the axis 25 of the one thread 23 runs coaxially to the axis 20 of the bone screw 13 and the axis 26 of the second thread 24 runs at an acute angle β to the axis 20 of the bone screw 13. Through the different threads 23, 24 which are cut on and/or over each other, individual parts of the threads are removed so that the thread elements 21, 22 remain as fastening elements 15 in the form of cams 16, 17.

At least one thread 27 is provided in the through hole 12 of the implant 11. In addition, the through hole 12 of the implant 11 is conically formed on both sides of the implant 11.

LIST OF REFERENCE NUMBERS

01 Implant
02 Through hole
03 Bone screw
04 Head
05 Fastening element
06 Cam
07 Cam
08 Slit
09 Shaft
10 Axis
11 implant
12 Through hole
13 Bone screw
14 Head
15 Fastening element
16 Cam
17 Cam
18 Slit
19 Shaft
20 Axis
21 Thread element
22 Thread element
23 Thread
24 Thread
25 Axis
26 Axis
27 Thread

The invention claimed is:

1. A fixation device for bones comprising an implant to be fastened to the bone having at least one through hole, and at least one bone screw to be fastened in said through hole having a screw thread for the bone, with fastening elements being arranged in the through hole of the implant and at the upper end of the bone screw which engage with each other, characterized in that the head of the bone screw has at least two threads, whereby the axis of the one thread runs coaxially to the axis of the bone screw and the axis of the other thread runs at an acute angle to the axis of the bone screw, and in that provided as fastening elements of the head of the bone screw are cams which are formed from thread elements of the at least two threads which engage with the fastening elements on the associated surfaces of the through hole of the implant.

2. The fixation device in accordance with claim 1 characterised in that at least one thread is provided in the through hole of the implant.

3. The fixation device in accordance with claim 1 characterised in that the through hole of the implant is conically designed on both sides of the implant.

* * * * *